(12) United States Patent
Gutierrez-Wing et al.

(10) Patent No.: US 10,602,670 B2
(45) Date of Patent: Mar. 31, 2020

(54) SELF-POWERED LIGHTS FOR PHOTOSYNTHETIC CULTURES

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Maria Teresa Gutierrez-Wing, Baton Rouge, LA (US); Jin-Woo Choi, Baton Rouge, LA (US)

(73) Assignee: BOARD OF SUPERVISORS OF LOUISANA STATE UNIVERSITY AND AGRICULTURE AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 15/766,189

(22) PCT Filed: Oct. 7, 2016

(86) PCT No.: PCT/US2016/055947
§ 371 (c)(1),
(2) Date: Apr. 5, 2018

(87) PCT Pub. No.: WO2017/062743
PCT Pub. Date: Apr. 13, 2017

(65) Prior Publication Data
US 2018/0295786 A1    Oct. 18, 2018

Related U.S. Application Data

(60) Provisional application No. 62/238,274, filed on Oct. 7, 2015.

(51) Int. Cl.
*A01G 7/04*    (2006.01)
*A01K 63/06*    (2006.01)
(Continued)

(52) U.S. Cl.
CPC .............. *A01G 7/045* (2013.01); *A01K 63/06* (2013.01); *B63B 22/00* (2013.01);
(Continued)

(58) Field of Classification Search
CPC ...... A01G 7/045; A01K 63/06; A01K 63/042; F21W 2131/308; F21Y 2115/10;
(Continued)

(56) References Cited

U.S. PATENT DOCUMENTS 5,089,945 A    2/1992    Mula
5,571,506 A    11/1996   Regan et al.
(Continued)

FOREIGN PATENT DOCUMENTS

JP    2016181261 A    * 10/2016    ............. G06F 3/044

OTHER PUBLICATIONS

Machine English Translation of JP2016181261-A; Hirakata, Yoshiharu (Year: 2016).*
(Continued)

*Primary Examiner* — Anh T Mai
*Assistant Examiner* — Glenn D Zimmerman
(74) *Attorney, Agent, or Firm* — Thomas | Horstemeyer, LLP

(57) ABSTRACT

Various examples of methods and systems are provided for increasing productivity of one or more photosynthetic cultures via self-powered light systems. In one example, a system includes a waterproof casing and a light module enclosed within the waterproof casing. The waterproof casing is configured to be neutrally buoyant in a culture tank comprising the one or more photosynthetic cultures. In another example, a method includes placing a self-powered light system within a culture tank, the self-powered light system being neutrally buoyant within the culture tank. The method further includes causing turbulence of water within (Continued)

the culture tank, and the self-powered light system harvests energy to power a light of the self-powered light system via the turbulence of the water within the culture tank.

20 Claims, 5 Drawing Sheets

(51) Int. Cl.
*B63B 22/00* (2006.01)
*F21Y 115/10* (2016.01)
*F21W 131/308* (2006.01)

(52) U.S. Cl.
CPC .... *F21W 2131/308* (2013.01); *F21Y 2115/10* (2016.08); *Y02E 10/38* (2013.01)

(58) Field of Classification Search
CPC ............ Y02E 10/38; B63B 22/00; F21S 9/02; C12M 31/10
See application file for complete search history.

(56) References Cited

U.S. PATENT DOCUMENTS

| | | | |
|---|---|---|---|
| 2005/0066654 A1 | 3/2005 | Koivusaari | |
| 2011/0157878 A1* | 6/2011 | Lai | F21S 9/037 362/183 |
| 2011/0215580 A1 | 9/2011 | Lu et al. | |
| 2013/0174792 A1 | 7/2013 | Delabbio | |
| 2014/0011245 A1* | 1/2014 | Flynn | C12M 21/02 435/134 |
| 2015/0055339 A1* | 2/2015 | Carr, Jr. | F21V 33/0044 362/234 |
| 2016/0010619 A1* | 1/2016 | Phillips | F03B 13/16 290/53 |
| 2016/0282989 A1* | 9/2016 | Hirakata | G06F 3/044 |
| 2017/0137764 A1* | 5/2017 | Punchard | C12M 21/02 |
| 2019/0185796 A1* | 6/2019 | Punchard | C12M 21/02 |

OTHER PUBLICATIONS

PCT International Search Report in co-pending, related PCT Application No. PCT/US2016/055947, dated Dec. 29, 2016.
Schnepf, R, Yacobucci, BD. Renewable Fuel Standard (RFS): Overview and Issues. Congressional Research Service. R40155. 33 p. p. 2010.
U.S. Department of Energy. National Algal Biofuels Technology Roadmap. DOE Biomass Program. DOE/EE-0332. P. 2010.
Pienkos, PT, Darzins, A. The promise and challenges of microalgal derived biofuels. Biofuels, Bioproducts and 3iorefining, 3[4]: 431-440.2009.
Schulze, PSC, Barreira, LA, Pereira, HGC, Perales, JA, Varela, JCS. Light emitting diodes (LEDs) applied to microalgal production. Trends in Biotechnology, 32[8]: 422-430. 2014.
Blanken, W, Cuaresma, M, Wijffels, RH, Janssen, M. Cultivation of microalgae on artificial light comes at a cost. Algal Research, 2[4]: 333-340.2013.
Silaban, A, Bai, R, Gutierrez-Wing, MT, Negulescu, II, Rusch, KA. Effect of organic carbon, C:N. ratio and light on the growth and lipid productivity of microalgae/cyanobacteria coculture. Engineering in Life Sciences, 14[1]: 47-56.2014.
Gutierrez-Wing, MT, Benson, BC, Rusch, KA. Impact of light quality and quantity on growth rate kinetics of the microalgae Selenastrum capricornutum. Engineering in Life Sciences, 11[5]: 1-10.2011.
Beeby, SP, Tudor, MJ, White, N. Energy harvesting vibration sources for microsystems applications. Measurement science and technology, 17[12]: R175. 2006.
Mitcheson, PD, Yeatman, EM, Rao, GK, Holmes, AS, Green, TC. Energy harvesting from human and machine motion or wireless electronic devices 2008.
Beeby, SP, Torah, R, Tudor, M, Glynne-Jones, P, O'Donnell, T, Saha, C, Roy, S. A micro electromagnetic generator for vibration energy harvesting. Journal of Micromechanics and microengineering, 17[7]: 1257. 2007.
11. d'Ippolito, G, Sardo, A, Paris, D, Vella, FM, Adelfi, MG, Botte, P, Gallo, C, Fontana, A. Potential of lipid metabolism in marine diatoms for biofuel production. Biotechnology for biofuels, 8[1]: 28. 2015.
Yeh, K-L, Chang, et al., Effect of light supply and carbon source on cell growth and cellular composition of a newly isolated microalga Chlorella vulgaris ESP-31. Engineering in Life Sciences, 10[3]: 201-208. 2010.
Shu, C-H, Huang, C-K, Tsai, C-C. Effects of light wavelength and intensity on the production of ethanol bySaccharomyces cerevisiaein batch cultures 2009.
Bold, HC. The cultivation of algae. The Botanical Review, 8[2]: 69-138. 1942.

* cited by examiner

SELF-POWERED LIGHTS FOR PHOTOSYNTHETIC CULTURES

CROSS-REFERENCE TO RELATED APPLICATION

This application is the 35 U.S.C. § 371 national stage application of PCT Application No. PCT/US2016/055947, filed Oct. 7, 2016, where the PCT claims priority to, and the benefit of, U.S. provisional application entitled "SELF-POWERED LIGHTS FOR PHOTOSYNTHETIC CULTURES" having Ser. No. 62/238,274, filed Oct. 7, 2015, both of which are hereby incorporated by reference in their entireties.

BACKGROUND

The interest over photosynthetic microbes such as microalgae and cyanobacteria as a source of bioproducts has expanded significantly in the last years. This interest has been promoted by the price fluctuations and security risks associated with fossil fuels. The need to reduce costs of fuels has promoted the interest in other microalgal bioproducts that can be even more attractive economically than the biofuels. These products can include pharmaceuticals, nutraceuticals, fertilizers, feeds, food additives, and pigments among others.

Although the microalgal productivity is higher than that of other crops, with up to 2,470-12,345 gal oil (hectare·yr)$^{-1}$, there are some limitations that need to be addressed to make it competitive. One of the major bottlenecks in the use of biofuels and other bioproducts is the availability of light[1-3]. In cultures maintained outdoors, that use available natural light, the depth and hence the productivity of the culture is limited by the light penetration and availability in a given area. For cultures maintained with artificial light, the energy for illumination can be a significant part of the cost of microalgal biomass production, reaching in some cases 50% or more of the costs[4-7]. Besides the light quantity, the wavelength distribution also affects the microalgal biomass production. It has been found that the wavelength affects not only the biomass productivity, but also its composition.

Several strategies have been explored to reduce the cost of light and increase the areal productivity of the microalgae. Among these strategies are thin layer photobioreactors, stacked reactors with waveguides, tubular photobioreactors, submerged light strips and many others. None of these methods overcome the basic lighting problems: 1) for cultures using natural light, the fixed limited availability of light energy per unit of area, the diurnal cycle (night/day) and the depth of light penetration; and 2) for cultures with artificial light, the cost of the electrical energy to provide illumination and the light penetration.

SUMMARY

Embodiments of the present disclosure are related to self-powered light systems used for the culture of photosynthetic organisms that are configured to harvest energy from water movement.

In one embodiment, among others, a system for increasing productivity of one or more photosynthetic cultures comprises a waterproof casing and a light module enclosed within the waterproof casing. The waterproof casing is configured to be neutrally buoyant in a culture tank comprising the one or more photosynthetic cultures. In one or more aspects of these embodiments, the light module can comprise a light-emitting diode (LED) and a battery, and the LED is powered by the battery. In one or more aspects of these embodiments, the light module can comprise an LED and a power harvesting device, and the LED is powered by the power harvesting device. In one or more aspects of these embodiments, the power harvesting device can comprise one or more electromagnetic components. In one or more aspects of these embodiments, the power harvesting device can comprise one or more piezoelectric components. In one or more aspects of these embodiments, the power harvesting device can be operable at low ambient motion frequency. In one or more aspects of these embodiments, the power harvesting device can harvest energy in response to movement of the waterproof casing caused by water turbulence in the culture tank. The water turbulence can be caused by aeration. The water turbulence can be caused by mechanical agitation. The water casing can be transparent. In one or more aspects, at least a portion of the light module can comprise at least one of a florescent paint or a florescent dye.

In another embodiment, among others, a method comprises placing a self-powered light system within a culture tank, the self-powered light system being neutrally buoyant within the culture tank and causing turbulence of water within the culture tank. The self-powered light system harvests energy to power a light of the self-powered light system via the turbulence of the water within the culture tank. In one or more aspects of these embodiments, the culture tank can comprise one or more photosynthetic cultures. In one or more aspects of these embodiments, the light can comprise a light-emitting diode (LED), and the self-powered light system can further comprise a power harvesting device that is configured to harvest the energy via the turbulence of the water.

In another embodiment, among others, a system comprises a culture tank having one or more photosynthetic cultures, and a self-powered light system disposed within the culture tank, the self-powered light system being neutrally buoyant within the culture tank. In one or more aspects of these embodiments, the self-powered light system comprises a power harvesting device coupled to a light-emitting diode (LED) enclosed in a waterproof casing. In one or more aspects of these embodiments, the waterproof casing can be transparent. In one or more aspects of these embodiments, the power harvesting device comprises one or more electromagnetic components. In one or more aspects of these embodiments, the power harvesting device comprises one or more piezoelectric components. In one or more aspects of these embodiments, the power harvesting device harvests energy to power the LED via movement of the self-powered light system caused by at least turbulence of water within the culture tank. In one or more aspects of these embodiments, the turbulence of the water is caused via aeration. In one or more aspects of these embodiments, the turbulence of the water is caused via mechanical agitation. In one or more aspects of these embodiments, at least a portion of the self-powered light system comprises at least one of a florescent paint or a florescent dye.

Other devices, systems, methods, features, and advantages of the present disclosure will be or become apparent to one with skill in the art upon examination of the following drawings and detailed description. It is intended that all such additional devices, systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views

FIG. 4A illustrates the power harvesting device with electromagnetic components. FIG. 4B illustrates the power harvesting device with piezoelectric components.

DETAILED DESCRIPTION

Figure 1:
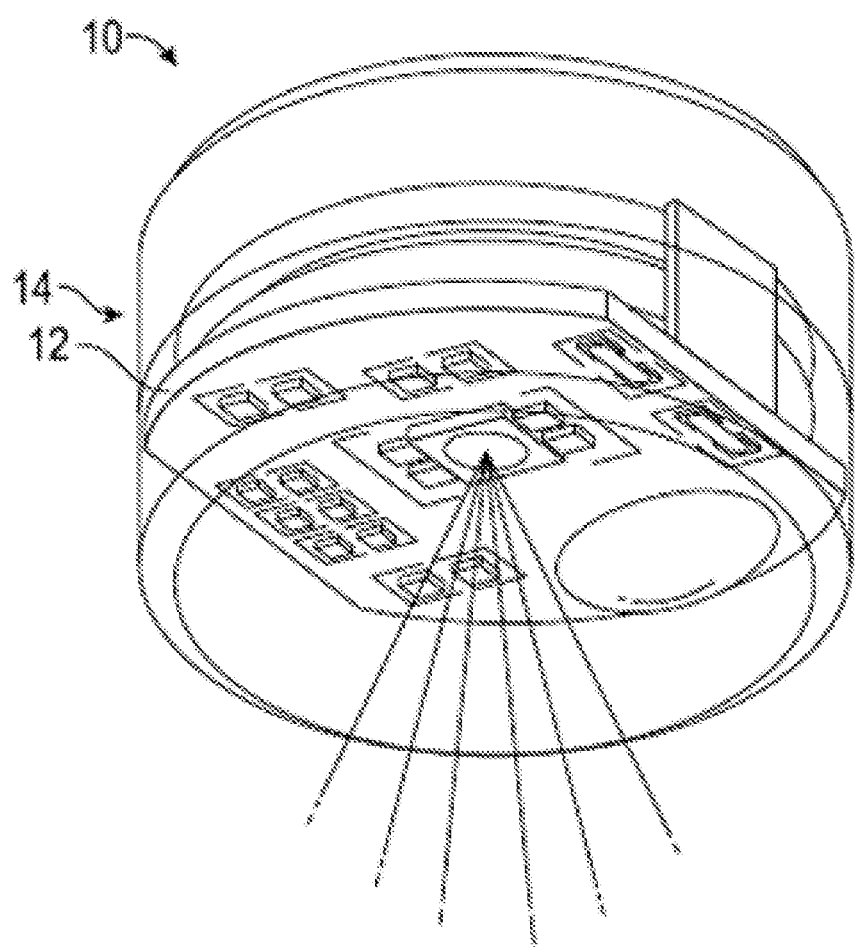
FIG. 1 is an example of a perspective view of a light system according to various embodiments of the present disclosure.

Disclosed herein are systems and methods for a self-powered light system used for the culture of photosynthetic organisms that are configured to harvest energy from water movement in a culture tank. Reference will now be made in detail to the description of the embodiments as illustrated in the drawings, wherein like reference numbers indicate like parts throughout the several views. This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

The following examples are put forth so as to provide those of ordinary skill in the art with a complete disclosure and description of how to perform the methods and use the structures disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

While embodiments of the present disclosure are described in connection with the corresponding text and figures, there is no intent to limit the disclosure to the embodiments in these descriptions. On the contrary, the intent is to cover all alternatives, modifications, and equivalents included with the spirit and scope of embodiments of the present disclosure.

Convention light systems for the culture of photosynthetic organisms are known to have the following lighting problems: 1) for cultures using natural light, there is fixed limited availability of light energy per unit of area, the diurnal cycle (night/day) and the depth of light penetration; and 2) for cultures with artificial light, there is the cost of the electrical energy to provide illumination and the light penetration.

The present disclosure addresses these problems through a self-powered light-emitting diode (LED) based neutral buoyancy light system. The light system of the present disclosures yields a self-powered light source that can be used in microalgal/cyanobacterial cultures to increase their productivity and reduce the limitation of culture depths. The light system comprises one or more buoyant units that each integrate an energy harvesting device that takes advantage of the movement needed to maintain the cultures in suspension, coupled with an efficient LED-based light that can be fine-tuned to deliver the light in the wavelength that can be more efficiently utilized by the target species to obtain the desired products.

Energy scavenging and harvesting from the surrounding environment can possibly eliminate the use of battery, which reduces cost for maintenance and environmental pollution caused by discarded batteries, while enabling self-sustainable device applications such as a sensor network. Although a solar cell is a well-known energy harvesting device, it is not practical for the current application. As an alternative, ambient motion and vibration can be a promising and abundant source of energy if converted into electricity[8]. Over the past few years, there have been research efforts in developing a small scale energy harvesting device from high frequency vibrations or resonance caused by mechanical systems or automobiles[9,10]. Nevertheless, in real world applications, harvesting energy from low frequency motions is more important and useful for wearable/portable electronic devices, oceanic and environmental monitoring sensor networks, and other outdoor or military uses. The scavenged energy will usually be small, but can be suitable for small scale electronic sensors and low power LED lighting.

The light system of the present disclosure can harvest energy from the water movement required to maintain the algal culture in suspension. Conventional systems depend on electricity to obtain their power, either in the form of rechargeable systems or directly plugged to an outlet. The self-powered lights of the present disclosure reduce the electricity consumption for illumination to a minimum. According to various embodiments of the present disclosure, the light sources are not attached to the culture structure, but are dispersed throughout the whole depth of the culture. Conventional artificial lighting available options either hang on top of the cultures or are submerged in fixed positions in arrays of many lights. The dispersed, neutrally buoyant lights of the present disclosure remove the limitation of the culture depth and can be reused continuously. Additionally, the light system units of the present disclosure do not require any special infrastructure or installation. The light system units can be used in any shape of tank, including raceways, ponds, or bioreactors. Conventional offerings must be calculated according to the geometry and capacity of the culture system.

The light system of the present disclosure can be used for the culture of any photosynthetic organism, such as, for example, microalgae, cyanobacteria, diatoms, filamentous algae, and/or others. The concentration of bioproducts of the microalgal/cyanobacterial biomass can be manipulated through the use of lights with different wavelength distributions (e.g., lights around 620-700 nm or around the 400-480 range can increase growth rates in some species, while in ranges of about 490-550 can increase the chlorophyll content). Lights of different colors can impact the concentration and type of pigments and lipids produced by microalgae[4,6,12,13]. The light system of the present disclosure can be expanded to cultures in environments that have limited or no natural light, such as, for example, closed reactors, underground facilities, deep culture systems and/or other systems that cannot be accommodated with traditional methods. In various embodiments, the light system of the present disclosure can be used as the sole light system or as a complement to other illumination strategies, such as, for example, natural light, overhead light and/or others, with little to no energy cost.

FIG. 1 provides an example of the light system according to various embodiments of the present disclosure. The light system of the present disclosure comprises one or more units 10 comprising a light module 12 disposed within enclosed in a sealed waterproof casing 14. As discussed in further detail with respect to FIG. 3, the light module 12 comprises a power source 16 coupled to a light source 18. The casing 14 of the light system unit 10 comprises a waterproof transparent casing sized to contain the light module 12. The casing 14 can comprise a transparent polymer material and/or other suitable material that is capable of being neutrally buoyant in the microalgal cultures. The light module 12 comprising the light source 18 and the power source 16 is disposed within the waterproof casing 14.

Figure 2:
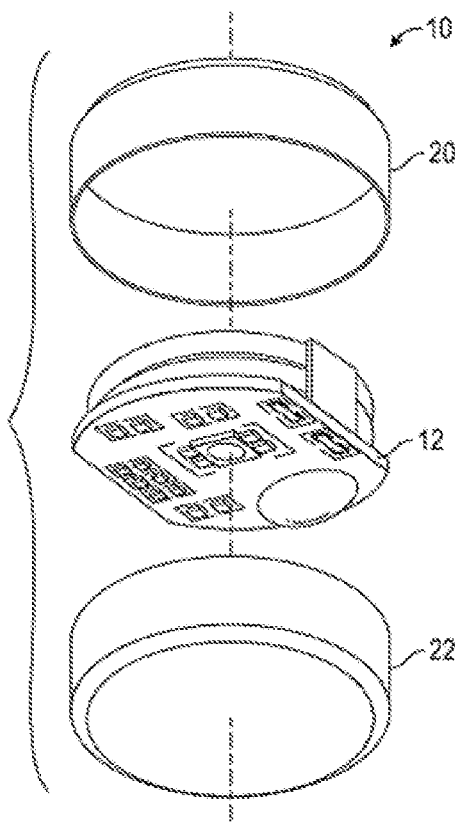
FIG. 2 is an example of an expanded view of the light system of FIG. 1 according to various embodiments of the present disclosure.

FIG. 2 illustrates an example of an expanded view of the light module 12 disposed within the casing 14. Specifically, FIG. 12 illustrates a top portion 20 of the casing and a bottom portion 22 of the casing 14 with the light module 12 disposed within. The top portion 20 and the bottom portion 22 are configured to connect to each other to form a sealed closure, thereby preventing liquid from being able to enter into the inside of the sealed casing 14. In some embodiments, an adhesive material may be disposed around the seam connecting the top portion 20 to the bottom portion 22 to further ensure that the seal is secure, eliminating the ability for liquid to enter into the inside of the sealed casing 14.

Figure 3:
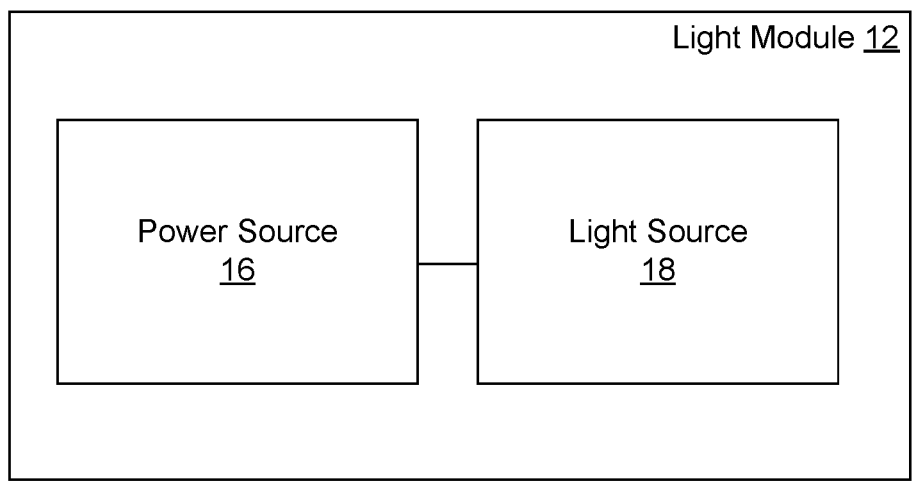
FIG. 3 is an example of a schematic representation of a light module of the light system of FIG. 1 according to various embodiments of the present disclosure.

Turning now to FIG. 3, shown is an example of a schematic representation of the light module 12 according to various embodiments of the present disclosure. The light module 12 comprises a power source 16 coupled to a light source 18. The light source 18 can comprise a light-emitting diode (LED) and/or other suitable light source. The power source 16 can comprise a power harvesting device 26 (FIGS. 4A-4B), a battery 28 (FIG. 6), a combination of a battery and a power harvesting device, and/or other appropriate power source. In some embodiments, the light source can be painted in part with fluorescent paint or dyes to adjust for the desired wavelengths as can be appreciated.

Figure 4A:
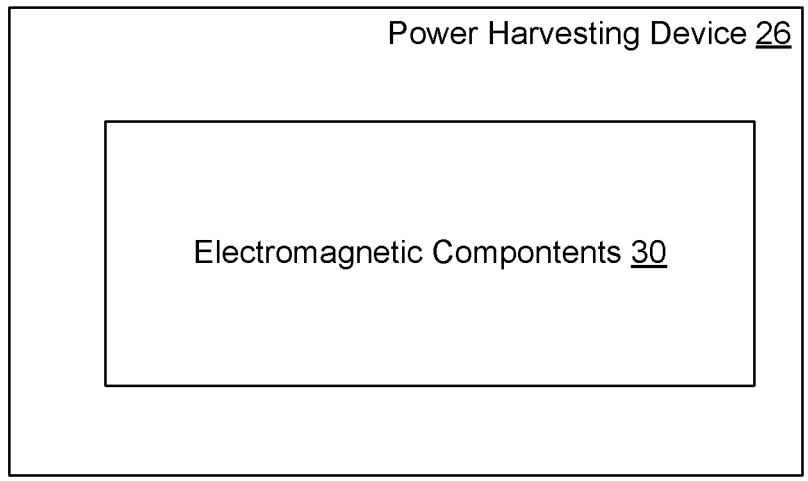
FIGS. 4A and 4B are examples of schematic representations of a power harvesting device of the light system of FIG. 1 according to various embodiments of the present disclosure.
Figure 4B:
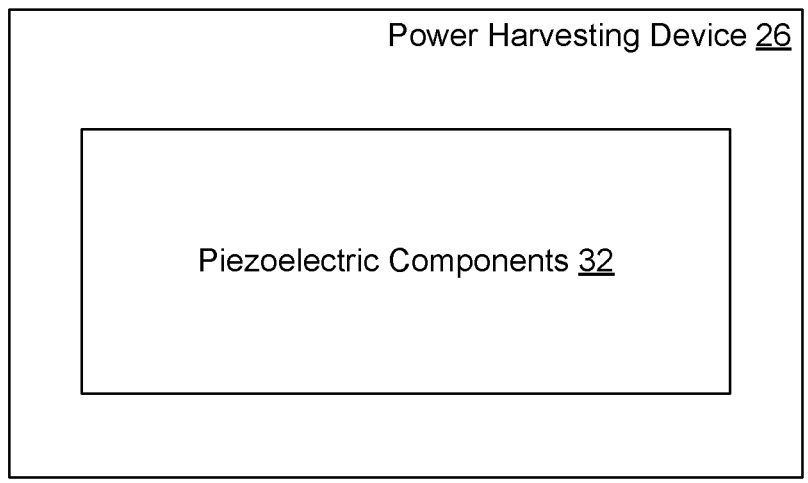

Moving on to FIGS. 4A-4B, shown is an example of a schematic representation of the power source 16 comprising the power harvesting device 26 according to various embodiments of the present disclosure. The power source 16 comprises a power harvesting device 26 that is configured to be operable at low ambient motion frequency (e.g., 0.1 Hz to 100 Hz). The power harvesting device 26 can be configured to be operable according to an electromagnetic scavenging method (FIG. 4A), a piezoelectric power scavenging method (FIG. 4B), and/or any other appropriate scavenging method. FIG. 4A illustrates the power harvesting device 26 comprising electromagnetic components 30 (e.g., generic electromagnetic coils, Faraday electromagnetic coil, Tesla electromagnetic coil, electrostatic electrodes, triboelectric electrodes, etc.) and FIG. 4B illustrates the power harvesting device 26 comprising piezoelectric components 32 (e.g., piezoelectric films, piezoelectric nanowires, piezoelectric nanowire forest, etc.). Using either the electromagnetic components 30 or the piezoelectric components 32, the power harvesting device 26 is configured to generate energy from movement of the light system unit 10 and provide power to the light source 18.

In some embodiments, the power harvesting device 26 includes electromagnetic components 30 comprising a miniaturized torsion spring structure fabricated using a rapid prototyping technology and a small-size (e.g., about 3 mm in diameter and about 1 mm in thickness) magnet, such as, for example, a Neodymium magnets (NdFeB) and/or other appropriate rare earth magnet. The magnet can be used as the inertial mass and the magnet for electromagnetic induction. The power harvesting device 26 can further comprise micro-fabricated microcoils, a house-made coil, an off-the-shelf miniaturized coil and/or other appropriate coil.

In some embodiments, the power harvesting device 26 is sized at about 1 cm$^3$ (1 cm×1 cm×1 cm). As the electromagnetic induction provides an alternating current (AC), a simple rectifying circuit with a charge storage device (e.g., capacitor) will be necessary to obtain a direct current (DC) electric power to power the light source. Since the scavenged voltage can be ultra-low, a conventional rectifying and regulating circuit may not be suitable to overcome power management concerns.

Figure 5:
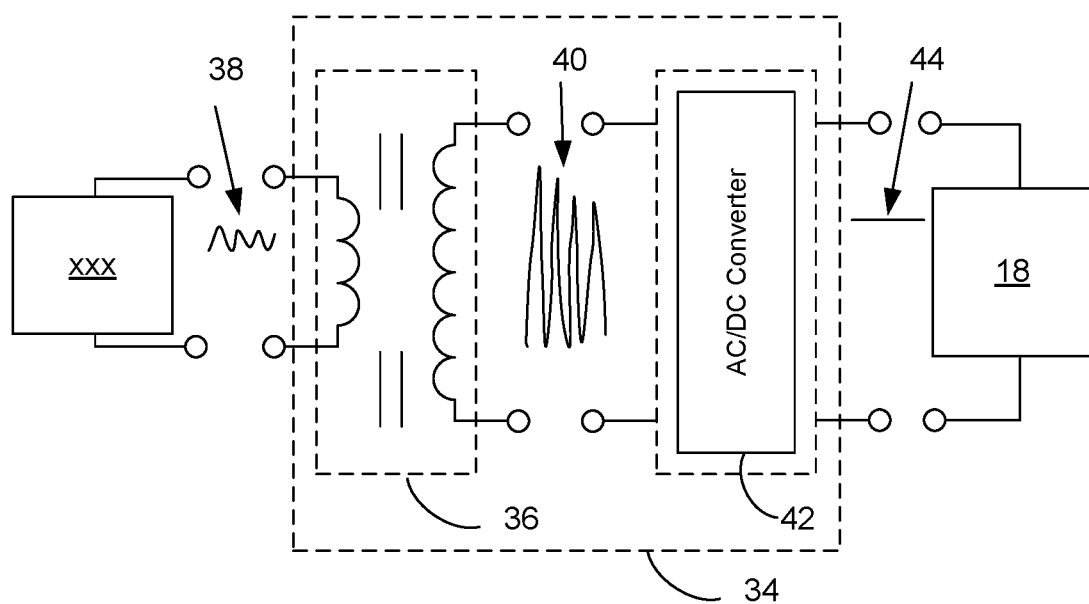
FIG. 5 illustrates an example of a schematic representation of rectifying circuit of the light system of FIG. 1 according to various embodiments of the present disclosure.

FIG. 5 illustrates an example of a simple rectifying circuit 34 showing a two-step voltage conversion for ultralow voltage conversion. The first step of the two-step voltage conversion is an AC/AC voltage step-up using a microtransformer 36 to boost the incoming AC signal 38 up to about 500~1,000 mV or in tenfold. The amplified signal 40 will then be fed to a surface mountable electronic voltage converter circuit 42 to generate a DC output voltage 44 that can be used to power up a light source 18. In some embodiments, the power source 16 comprises the harvesting device 26 and a battery 28 in combination. In some embodiments, the battery 28 can be rechargeable, and the DC output voltage 44 may be used to charge the battery 28 which is then used to power the light source 18.

In an experiment, a power rectifying circuit 34 with an IC (e.g., LTC3109 from Linear Technology Corp., Milpitas, Calif.) was tested to rectify a simulated AC current. The results show that the rectifying circuit 34 can produce an output DC voltage up to about 4.1 V with an alternating AC voltage input, which is enough to turn on the light source 18. The fabricated device can be characterized at various conditions of motion frequency (ambient motion) and applied acceleration (or inertial force) mimicking real world events. The power generation can be in microwatts (μW) range, but it is possible to further improve the power level by optimizing resonator structures and dimensions.

Figure 6:
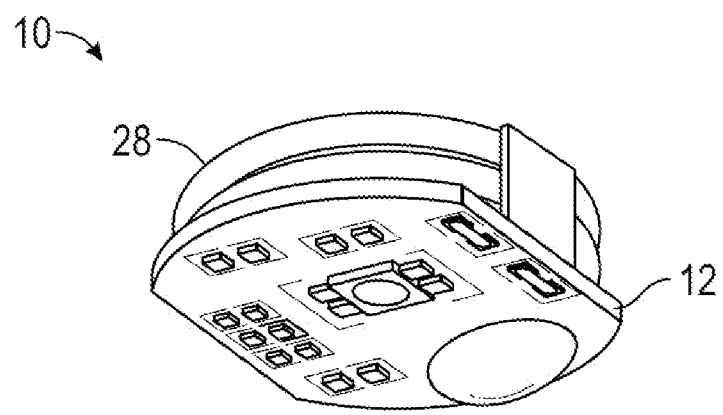
FIG. 6 illustrates a perspective view of an example light module of the light system of FIG. 1 where the power source includes a battery according to various embodiments of the present disclosure.

While the preferred embodiment of the power source 16 comprises a power harvesting device 26 that harvests energy from related to ambient motion (e.g. movement of unit in culture tank) and/or applied acceleration (e.g., inertial force), the power source 16 can comprise a battery 28 according to various embodiments. FIG. 6 illustrates a light module 12 comprising a battery 28 powering a light source 18.

Figure 7:
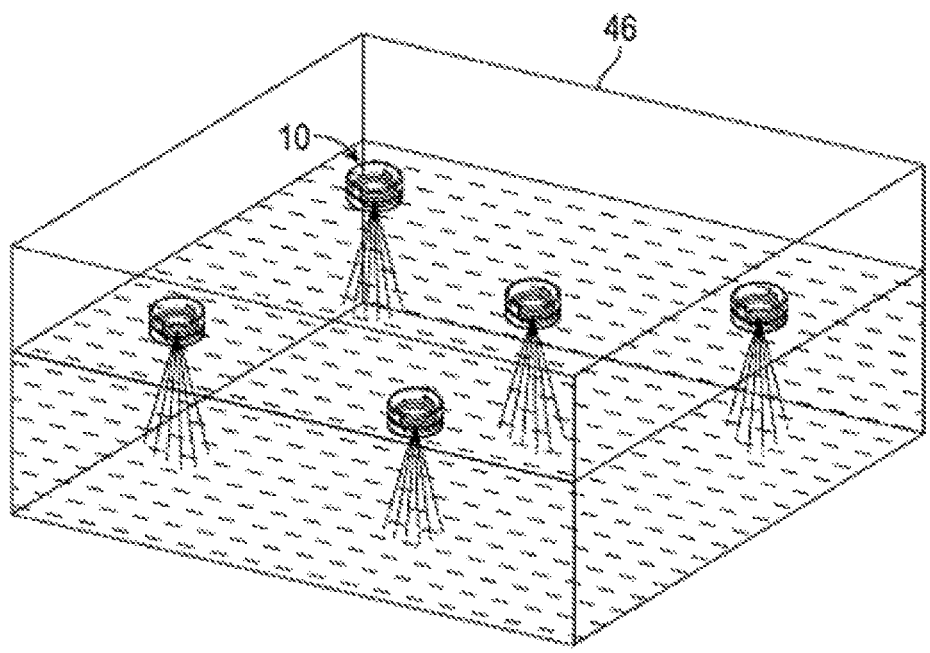
FIG. 7 illustrates a perspective view of the light system of FIG. 1 disposed within a culture tank according to various embodiments of the present disclosure.

FIG. 7 shows an example of the light system units 10 of the present disclosure disposed within a culture tank 46 according to various embodiments of the present disclosure. The culture tank 46 comprises any type and shape of culture tank as can be appreciated, including raceways, ponds, or bioreactors. The light system units 10 can free float with cultures within a culture tank 46. The movement of the water within the culture tank 46 may be caused by vigorous aeration, mechanical agitation (e.g., paddles), and/or other suitable method to produce appropriate turbulence for algal cultures. As the light system unit moves in response to the movement of the water, the power source 16 generates the energy, via the ambient energy of the unit, used to power the light source 18.

It has been well documented that the type and intensity of light affects the growth and composition of the microalgal/cyanobacterial cultures. To test the effect of the suspended light system units 10 of the present disclosure, a microalgal and cyanobacterial species of interest can be inoculated in the culture tank 46, to an optical density of 0.1. The culture can be maintained in Bold's Basal medium[14] until the optical density reaches a plateau. The growth rate can be estimated based on the optical density. A calibration curve of optical density vs dry biomass can be prepared to estimate the biomass increase with time. Pigment content (Chlorophyll or phycocyanin, depending on the species selected) can be measured by spectrophotometric and/or fluorescence methods. The biomass and lipid productivity can be estimated. The effect of the biomass density on the light distribution and intensity can be measured. The results of this task can indicate, as appreciated, the number and intensity of suspended lights needed, based in the culture density and growth rate. Optical density can be measured with a spectrophotometer at a wavelength of 640 nm (HACH 6000). Nutrients can be measured with spectrophotometric methods (HACH 6000). The pH, temperature, and ORP can be measured with a probe (HACH).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

REFERENCES

[1] Schnepf, R, Yacobucci, B D. *Renewable Fuel Standard (RFS): Overview and Issues*. Congressional Research Service. R40155. 33 p. p. 2010.

[2] U.S. Department of Energy. *National Algal Biofuels Technoology Roadmap. DOE Biomass Program*. DOE/EE-0332. P. 2010

[3] Pienkos, P T, Darzins, A. The promise and challenges of microalgal derived biofuels. *Biofuels, Bioproducts and Biorefining*, 3[4]: 431-440. 2009.

[4] Schulze, P S C, Barreira, L A, Pereira, H G C, Perales, J A, Varela, J C S. Light emitting diodes (LEDs) applied to microalgal production. *Trends in Biotechnology*, 32[8]: 422-430. 2014.

[5] Blanken, W, Cuaresma, M, Wijffels, R H, Janssen, M. Cultivation of microalgae on artificial light comes at a cost. *Algal Research*, 2[4]: 333-340. 2013.

[6] Silaban, A, Bai, R, Gutierrez-Wing, M T, Negulescu, I I, Rusch, K A. Effect of organic carbon, C:N ratio and light on the growth and lipid productivity of microalgae/cyanobacteria coculture. *Engineering in Life Sciences*, 14[1]: 47-56. 2014.

[7] Gutierrez-Wing, M T, Benson, B C, Rusch, K A. Impact on light quality and quantity on growth rate kinetics of the microalgae Selenastrum capricornutum. *Engineering in Life Sciences*, 11[5]: 1-10. 2011.

[8] Beeby, S P, Tudor, M J, White, N. Energy harvesting vibration sources for microsystems applications. *Measurement science and technology*, 17[12]: R175. 2006.

[9] Mitcheson, P D, Yeatman, E M, Rao, G K, Holmes, A S, Green, T C. Energy harvesting from human and machine motion for wireless electronic devices. *Proceedings of the IEEE*, 96[9]: 1457-1486. 2008.

[10] Beeby, S P, Torah, R, Tudor, M, Glynne-Jones, P, O'Donnell, T, Saha, C, Roy, S. A micro electromagnetic generator for vibration energy harvesting. *Journal of Micromechanics and microengineering*, 17[7]: 1257. 2007.

[11.] d'Ippolito, G, Sardo, A, Paris, D, Vella, F M, Adelfi, M G, Botte, P, Gallo, C, Fontana, A. Potential of lipid metabolism in marine diatoms for biofuel production. *Biotechnology for biofuels*, 8[1]: 28. 2015.

[12.] Shu, C-H, Huang, C-K, Tsai, C-C. Effects of light wavelength and intensity on the production of ethanol by Saccharomyces cerevisiaein batch cultures. *Journal of Chemical Technology & Biotechnology*, 84[8]: 1156-1162. 2009.

[13.] Yeh, K-L, Chang, J-S, chen, W-m. Effect of light supply and carbon source on cell growth and cellular composition of a newly isolated microalga Chlorella vulgaris ESP-31. *Engineering in Life Sciences*, 10[3]: 201-208. 2010.

[14.] Bold, H C. The cultivation of algae. *The Botanical Review*, 8[2]: 69-138. 1942.

We claim at least the following:

1. A system for increasing productivity of one or more photosynthetic cultures, comprising:
    a waterproof casing; and
    a light module enclosed within the waterproof casing,
    wherein the light module comprises an LED and a power harvesting device, the LED being powered by the power harvesting device,
    wherein the power harvesting device harvests energy in response to movement of the waterproof casing caused by water turbulence in the culture tank, and
    wherein the waterproof casing is configured to be neutrally buoyant in a culture tank comprising the one or more photosynthetic cultures.

2. The system of claim 1, wherein the light module comprises a battery.

3. The system of claim 1, wherein the power harvesting device comprises one or more electromagnetic components.

4. The system of claim 1, wherein the power harvesting device comprises one or more piezoelectric components.

5. The system of claim 1, wherein the power harvesting device is operable at low ambient motion frequency.

6. The system of claim 1, wherein the water turbulence is caused by aeration.

7. The system of claim 1, wherein the water turbulence is caused by mechanical agitation.

8. The system of claim 1, wherein the waterproof casing is transparent.

9. The system of claim 1, wherein at least a portion of the light module comprises at least one of a florescent paint or a florescent dye.

10. A method, comprising,
    placing a self-powered light system within a culture tank, the self-powered light system being neutrally buoyant within the culture tank; and
    causing turbulence of water within the culture tank,
    wherein the self-powered light system harvests energy to power a light of the self-powered light system via the turbulence of the water within the culture tank.

11. The method of claim 10, wherein the culture tank comprises one or more photosynthetic cultures.

12. The method of claim 10, wherein the light comprises a light-emitting diode (LED), and the self-powered light system further comprises a power harvesting device that is configured to harvest the energy via the turbulence of the water.

13. The method of claim 10, wherein the turbulence is caused by aeration.

14. The method of claim 10, wherein the turbulence is caused by mechanical agitation.

15. A system, comprising:
    a culture tank comprising one or more photosynthetic cultures; and
    a self-powered light system disposed within the culture tank, the self-powered light system being neutrally buoyant within the culture tank,
    wherein the self-powered light system comprises a power harvesting device coupled to a light-emitting diode (LED) enclosed in a waterproof casing, and
    wherein the power harvesting device harvests energy to power the LED via movement of the self-powered light system caused by at least turbulence of water within the culture tank.

16. The system of claim 15, wherein the power harvesting device comprises at least one of: one or more electromagnetic components or one or more piezoelectric components.

17. The system of claim 15, wherein the turbulence of the water is caused via aeration or mechanical agitation.

18. The system of claim 15, wherein at least a portion of the self-powered light system comprises at least one of a florescent paint or a florescent dye.

19. The system of claim 15, wherein the waterproof casing is transparent.

20. The system of claim 15, wherein the power harvesting device is operable at low ambient motion frequency.

* * * * *